United States Patent
Mabuchi et al.

(10) Patent No.: US 7,442,302 B2
(45) Date of Patent: Oct. 28, 2008

(54) HIGHLY WATER-PERMEABLE BLOOD PURIFIER OF HOLLOW-FIBER MEMBRANE TYPE

(75) Inventors: Kimihiro Mabuchi, Shiga (JP); Noriyuki Tamamura, Osaka (JP); Hidehiko Sakurai, Shiga (JP); Noriko Monden, Shiga (JP); Shinya Koyama, Shiga (JP); Hiroshi Shibano, Osaka (JP); Katsuaki Kuze, Shiga (JP); Katsuhiko Nose, Osaka (JP)

(73) Assignee: Toyo Boseki Kabushiki Kaisha, Osaka (JP)

(*) Notice: Subject to any disclaimer, the term of this patent is extended or adjusted under 35 U.S.C. 154(b) by 288 days.

(21) Appl. No.: 10/559,398

(22) PCT Filed: Aug. 26, 2004

(86) PCT No.: PCT/JP2004/012269
§ 371 (c)(1),
(2), (4) Date: Dec. 5, 2005

(87) PCT Pub. No.: WO2005/021068
PCT Pub. Date: Mar. 10, 2005

(65) Prior Publication Data
US 2006/0191844 A1 Aug. 31, 2006

(30) Foreign Application Priority Data
Aug. 29, 2003 (JP) ............................... 2003-209839

(51) Int. Cl.
*B01D 33/21* (2006.01)
*B01D 39/00* (2006.01)
*B01D 39/14* (2006.01)
*B01D 71/06* (2006.01)
*B01D 71/28* (2006.01)

(52) U.S. Cl. ........................... 210/500.23; 210/500.27; 210/500.42; 210/500.36; 210/500.41

(58) Field of Classification Search ............ 210/500.27, 210/500.23, 500.36, 500.41, 500.42; 264/41, 264/176.1, 178 R, 189
See application file for complete search history.

(56) References Cited

U.S. PATENT DOCUMENTS

| 5,340,480 A | * | 8/1994 | Kawata et al. ......... 210/500.23 |
| 5,849,189 A | | 12/1998 | Emi et al. |
| 2001/0004976 A1 | | 6/2001 | Kozawa et al. |

FOREIGN PATENT DOCUMENTS

| EP | 0 568 045 | 3/1993 |
|---|---|---|
| EP | 0 697 242 | 2/1996 |
| EP | 0 997 182 | 3/2000 |
| EP | 1 110 563 | 6/2001 |
| JP | 6-165926 | 6/1994 |
| JP | 2688564 | 8/1997 |
| JP | 2000-107577 | 4/2000 |
| JP | 2000-140589 | 5/2000 |
| JP | 2000-254222 | 9/2000 |
| JP | 2001-038170 | 2/2001 |
| JP | 3193262 | 5/2001 |
| JP | 2001-170171 | 6/2001 |
| JP | 2001-190934 | 7/2001 |
| JP | 3212313 | 7/2001 |
| JP | 3312838 | 5/2002 |

* cited by examiner

*Primary Examiner*—Ana M Fortuna
(74) *Attorney, Agent, or Firm*—Fish & Richardson P.C.

(57) ABSTRACT

The present invention provides a highly water permeable hollow fiber membrane type blood purifier for medical use, which is excellent in safety and module-assembling ease and which has a high water permeability suitable for use in therapy of chronic renal failure.

The present invention relates to a highly water-permeable hollow fiber type blood purifier comprising hydrophobic polymer hollow fiber membranes each of which contains a hydrophilic polymer, characterized in that the amount of the hydrophilic polymer eluted from the hollow fiber membrane is 10 ppm or less; in that the ratio of the hydrophilic polymer in the outer surface of the hollow fiber membrane is 25 to 50 mass %; in that the burst pressure of the hollow fiber membrane is 0.5 MPa or higher; and in that the coefficient of water permeability of the blood purifier is 150 ml/m$^2$/hr./mmHg or higher.

7 Claims, No Drawings

HIGHLY WATER-PERMEABLE BLOOD PURIFIER OF HOLLOW-FIBER MEMBRANE TYPE

FIELD OF THE INVENTION

The present application is filed claiming the priority based on Japanese Patent Application No. 2003-209839, and a whole of the contents of Japanese Patent Application No. 2003-209839 are incorporated herein by reference.

The present invention relates to a highly water permeable hollow fiber membrane type blood purifier for medical use, which is excellent in safety and module-assembling ease and which has a high water permeability suitable for use in therapy of chronic renal failure.

BACKGROUND OF THE INVENTION

In the hemocatharsis therapy for renal failure or the like, modules such as hemodialyzers, blood filters and hemodialyzer-filters, using dialysis membranes or ultrafilter membranes as separators are widely used to remove urine toxin and waste products from bloods. Dialysis membranes and ultrafilter membranes for use as separators are generally formed from natural materials such as cellulose or derivatives thereof (e.g., cellulose diacetate, cellulose triacetate and the like), and synthesized polymers such as polysulfone, polymethyl methacrylate, polyaclyronitrile and the like. Above all, highly importance is attached to modules using hollow fiber type membranes as separators in the field of dialyzers, because of the advantages thereof, such as the reduction of the volume of the extracorporeal-circulated blood, high waste product-removing rate, and high productivity of manufacturing modules.

The main use of a dialysis module using hollow fiber membranes is to remove low molecular weight substances such as urea, creatinine, etc. from blood by generally allowing the blood to flow into the internal voids of hollow fibers while allowing a dialyzate to flow opposing the blood outside the hollow fibers, and allowing the low molecular weight substances to diffuse and immigrate from the blood to the dialyzate, thereby removing the low molecular weight substances from the blood. With the increase in the number of patients undergoing therapies of dialysis over long periods of time, the dialysis complications have raised issues, and recently, the subject substances to be removed by dialysis are not only the low molecular weight substances such as urea and creatinine, but also medium molecular weight substances having molecular weights of several thousands and high molecular weight substances having molecular weights of 10,000 to 20,000. Under such a circumstance, hemocatharsis membranes are demanded to remove also these substances. Above all, β2 microglobulin having a molecular weight of 11,700 which is known to be a causal substance of carpal tunnel syndrome is a target to be removed. To obtain membranes for use in removal of such high molecular weight substances for therapy, it is preferable to increase the water permeability thereof by increasing the sizes of the holes of the dialysis membranes, increasing the number of the holes thereof, increasing the void content thereof or reducing the thickness thereof.

However, there is a problem in that the improvement of the water permeability induces the elution of more hydrophilic polymers, which leads to the lowered strength of the membranes. The elution of more and more hydrophilic polymers may induce side effects and complications since the hydrophilic polymers as foreign matters to human bodies are more and more accumulated in the human bodies over long periods of dialysis therapies. In addition, because of the decreased strengths of the membranes, the fibers thereof are damaged in the course of manufacturing, transporting or handling the same. As a result, the fibers tend to be broken during the therapy to cause the leakage of blood.

As the means for inhibiting the leakage of blood, there is disclosed a technique for seeking proper time during which a spinning dope extruded from a nozzle passes through a gaseous phase, and a proper range of the concentration of a core material, by further decreasing the concentration of an organic solvent in the core material (cf. Patent literature 1). This is a method of forming a thin and dense layer on the inner surface of a membrane while controlling the water permeability of the membrane. However, this method has difficulties in that the water permeability of the membrane is hard to be set within a narrow range, because the dense layer formed on the inner surface of the membrane markedly affects the water permeability of the membrane.

Further, the increasing of the hole sizes, the numbers of the holes or the percentage of void of membranes leads to more contents of hydrophilic polymers on the outer surfaces of the membranes. As a result, there is a high possibility of the invasion of endotoxin in a dialyzate, into blood to thereby induce side effects such as fever, etc. In another case, hollow fiber membranes stick to one another because of the hydrophilic polymers present on the outer surfaces of the membranes while the membranes are being dried, and therefore, the assembling of a module becomes hard.

A technique to solve the problem of the endotoxin's invasion into the blood, among the foregoing problems, is disclosed (cf. Patent Literature 2). This technique takes advantage of the properties of endotoxin which has a hydrophobic moiety in the molecule and thus tends to be adsorbed to a hydrophobic material. According to this technique, the ratio of a hydrophilic polymer to a hydrophobic polymer on the outer surface of a hollow fiber membrane is 5 to 25 mass %. While this technique is very preferable as a method of inhibiting the invasion of endotoxin into blood, it is needed to remove the hydrophilic polymer on the outer surface of the membrane by washing, in order to impart such a property to the membrane. This washing requires long time to treat the membrane, which results in low cost-effectiveness. For example, according to Examples of the above Patent Literature, a membrane is washed by showering hot water of 60° C. thereon for one hour, and washed with hot water of 110° C. for one hour.

Decreasing the amount of a hydrophilic polymer on the outer surface of a membrane is preferable to inhibit the invasion of endotoxin into blood. However, the hydrophilicity of the outer surface of the membrane becomes lower, which leads to a lower compatibility of the membrane with a normal saline solution which is used to wet a dried hollow fiber membrane bundle for assembling a module. Accordingly, purging the membrane of an air (priming) in the course of the wetting operation becomes insufficient. As a method of solving this problem, blending of a hydrophilic compound such as glyceline or the like is disclosed (cf. Patent Literature 3 and 4). However, this method has problems in that the hydrophilic compound acts as a foreign matter during dialysis if the concentration thereof is outside a proper range, and in that the susceptibility of the hydrophilic compound to photo-deterioration or the like gives an adverse influence on the storage stability of the module. There is a further problem in that, when a bundle of the hollow fiber membranes is fixed in a module for assembling the same, the bonding of an adhesive is hindered.

To avoid the sticking of the hollow fiber membranes to one another, i.e., another one of the foregoing problems, a method of increasing the rate of hole area of the outer surface of a membrane to 25% or more is disclosed (cf. Patent Literature 5). This method is surely preferred to avoid the sticking of the membranes, but has a problem in that the strength of the membrane becomes lower because of the higher rate of hole area. As a result, the leakage of blood as mentioned above occurs. A further disclosed method of avoiding this problem is to specify the rate of hole area or the hole area of the outer surface of a membrane (cf. Patent Literature 6). However, this method has a problem in that the water permeability of the membrane becomes lower.

Patent Literature 7 discloses a technique of suppressing, to 10 ppm or less, the elution of a hydrophilic polymer from a hydrophobic polymeric hollow fiber membrane which contains the hydrophilic polymer. However, this technique is accomplished, excluding the consideration of the hemodiafiltration which is demanded to have higher pressure resistance and higher endotoxin-removing performance than the conventional hemodialysis. For example, this literature has no teaching about the content of polyvinyl pyrrolidone on the outer surface of a membrane, and the burst pressure, the rate of hole area and the average hole area of the outer surface thereof. Particularly, there is no definite disclosure about the very important factors, i.e., the non-uniform section and the burst pressure of the membrane which is attributed to the flaws of the membrane.

Patent Literature 1: JP-A-2000-107577
Patent Literature 2: JP-A-2000-254222
Patent Literature 3: JP-A-2001-190934
Patent Literature 4: JP-B-3193262
Patent Literature 5: JP-A-2001-38170
Patent Literature 6: JP-A-2000-140589
Patent Literature 7: JP-A-2001-170171

DISCLOSURE OF THE INVENTION

Problem to be Solved by the Invention

An object of the present invention is to provide a medical hollow fiber type blood purifier having high water permeability, which is excellent in safety and module-assembling ease and is suitable for therapy of chronic renal failure.

Means for Solving the Problem

The present invention relates to a highly water permeable hollow fiber membrane type blood purifier which comprises hydrophobic polymeric hollow fiber membranes containing hydrophilic polymers, and which is characterized in that the amount of the hydrophilic polymer eluted from the hollow fiber membrane is 10 ppm or less; the ratio (or content) of the hydrophilic polymer in the outer surface of the hollow fiber membrane, 25 to 50 mass %; and the burst pressure of the hollow fiber membrane, 0.5 MPa or more; and in that the coefficient of water permeability of the blood purifier is 150 ml/m$^2$/hr./mmHg or more.

BEST MODES FOR CARRYING OUT THE INVENTION

The hollow fiber membrane to be used in the present invention comprises a hydrophobic polymer containing a hydrophilic polymer moiety. Examples of a material for the hydrophobic polymer of the present invention include cellulose resins such as regenerated cellulose, cellulose acetate and cellulose triacetate; polysulfone type resins such as polysulfone and polyether sulfone; polyacrylonitrile; polymethyl methacrylate; ethylene vinyl-alcohol copolymers; and the like. Above all, the cellulose type resins and the polysulfone type resins are preferable, since the use of these resins makes it easy to obtain hollow fibers having a coefficient of water permeability of 150 mL/m$^2$/hr./mmHg or more. More preferable are cellulose diacetate and cellulose triacetate among the cellulose type resins, and polyether sulfone among the polysulfone type resins, since the use of such resins makes it easy to reduce the thickness of membranes.

Although not particularly limited, the hydrophilic polymer to be preferably used in the present invention is such one that can form a micro phase-separated structure with the hydrophobic polymer in a solution. Specific examples of the hydrophilic polymer include polyethylene glycol, polyvinyl alcohol, carboxylmethyl cellulose, polyvinyl pyrrolidone and the like. The use of polyvinyl pyrrolidone is preferred in view of safety and cost-effectiveness.

In the present invention, the content of the hydrophilic polymer to the hydrophobic polymer in the membrane, or the content of the hydrophilic polymer based on the total of the hydrophobic polymer and the hydrophilic polymer in the membrane is within such a range as to be enough to impart sufficient hydrophilicity and high moisture content to the hollow fiber membrane. Preferably, the content of the hydrophobic polymer is 80 to 99 mass %, and that of the hydrophilic polymer, 1 to 20 mass %. When the content of the hydrophilic polymer to the hydrophobic polymer is too low, the hydrophilicity-imparting effect to the membrane may be poor. Therefore, the content of the hydrophilic polymer is preferably 2 mass % or more. On the other hand, when the above content is too high, the hydrophilicity-imparting effect is saturated, and the amount of the hydrophilic polymer eluted from the membrane tends to increase, and may exceed 10 ppm as will be described later. Therefore, the content of the hydrophilic polymer is more preferably 18 mass % or less, still more preferably 15 mass % or less, particularly 12 mass % or less, most preferably 9 mass % or less. The hollow fiber membrane of the present invention may contain a third component in addition to the hydrophobic polymer and the hydrophilic polymer, to an extent that the properties of the hollow fiber membrane suitable for use in a blood purifier are not impaired.

In the present invention, the amount of the hydrophilic polymer eluted from the hollow fiber membrane is preferably 10 ppm or less. When this amount exceeds 10 ppm, a side effect or a complication may be induced due to the eluted hydrophilic polymer if a patient undergoes a dialysis therapy over a long period of time. There is no limit in selection of a method of satisfying the above properties. For example, these properties can be obtained by restricting the content of the hydrophilic polymer to the hydrophobic polymer to the above specified range, or by optimizing the film-forming conditions for the hollow fiber membrane. The amount of the hydrophilic polymer eluted from the membrane is more preferably 8 ppm or less, still more preferably 6 ppm or less, particularly 4 ppm or less. This amount is preferably zero in view of safety to the organism. However, when the amount of the hydrophilic polymer eluted from the membrane is zero, the hydrophilicity of the surface of the membrane in contact with the blood becomes lower so that the compatibility of the membrane to the blood may be poor. Therefore, about 0.1 ppm or so of the hydrophilic polymer eluted from the membrane is allowed.

In one of the preferred embodiments of the present invention, the hydrophilic polymer is crosslinked to be insoluble. The method of crosslinking, the degree of crosslinking, etc.

are not limited. Crosslinking by γ-rays, electron rays or heat, chemical crosslinking or the like may be employed. Particularly, crosslinking by γ-rays or electron rays is preferable, because any residue such as an initiator does not remain and because the penetration of γ-rays or electron rays into the material is high. In the present invention, preferably, a module is charged with a degassed aqueous RO solution at high density and sealed, and is exposed to 10 to 60 kGY of γ-rays. When the dosage of γ-rays is too small, the crosslinking is insufficient to increase the amount of the eluted hydrophilic polymer. Therefore, it is preferable to expose the module to 15 or more kGy of γ-rays. When the dosage of γ-rays is too large, the hydrophobic polymer, the hydrophilic polymer, the housing and the urethane resin may be disintegrated and deteriorated. Thus, the dosage of γ-rays is preferably 50 kGy or less, more preferably 40 kGy or less, particularly 30 kGy or less. The degassed aqueous RO solution herein referred to means an aqueous RO solution which is obtained by heating the solution to a temperature of a room temperature to 50° C., and stirring the solution for 15 mins. to 2 hours while decompressing the same to −500 to −750 mmHg. When water, not degassed, is used, the oxygen dissolved in water oxidizes and deteriorates the components of the membrane, and consequently, the eluted components tend to increase.

In the present invention, the insolubilization is confirmed based on the solubility of the crosslinked membranes which are dipped in dimethylformamide. That is, 1.0 g of the crosslinked membranes are cut out and then are dipped in 100 ml of dimethylformamide so as to visually observe the presence of the insoluble components. In case of a module charged with a liquid, firstly, the liquid is removed; then, pure water is allowed to flow into a passage on the side of a dialyzate at a rate of 500 mL/min. for 5 minutes; and then, pure water is similarly allowed to flow into a passage on the side of the blood at a rate of 200 mL/min. for 5 minutes. Finally, pure water is allowed to pass through the membranes from the side of the blood to the side of the dialyzate at a rate of 200 mL/min. Thus, the washing of the module is completed. The hollow fiber membranes are removed from the resultant module, and then are freeze-dried for use as a sample which is to be used to measure insoluble components. Also, a module comprising dried hollow fiber membranes is similarly washed so as to be used as a sample.

In the present invention, the content of the foregoing hydrophilic polymer in the outer surface of the hollow fiber membrane is 25 to 50 mass %. When the content of the hydrophilic polymer in the outer surface of the membrane is too low, the content of the hydrophilic polymer in a whole of the membrane, particularly in the inner surface of the membrane becomes too low, which may lower the compatibility of the membrane with blood or the permeability of the membrane. When the dried membranes are used, the priming performance thereof tends to be low. When a hemodialyzer is used for hemocatharsis, the wetting and degassing of hollow fiber membranes by allowing physiological saline or the like to pass through the outer and inner portions of the hollow fiber membranes is needed. In this priming operation, it is considered that the roundness of the hollow fiber membranes, the crushing of the end portions thereof, the deformation thereof, the hydrophilicity of the material for the membranes and so on may give some influence on the priming performance of the membranes. When a module comprising dried hollow fiber membranes of a hydrophobic polymer and a hydrophilic polymer is used, the hydrophilic-hydrophobic balance in the hollow fiber membrane gives serious influence on the priming performance of the membranes. Accordingly, the content of the hydrophilic polymer is more preferably 27 mass % or more, still more preferably 30 mass % or more. When the content of the hydrophilic polymer in the outer surface of the membrane is too high, the possibility of the invasion of endotoxin in a dialyzate to the side of blood becomes higher to induce side effects such as fever; or the hollow fiber membranes stick to one another due to the hydrophilic polymer on the outer surfaces of the membranes, when the membranes are dried, so that the assembling of the module becomes hard. Therefore, the content of the hydrophilic polymer is more preferably 47 mass % or less, still more preferably 45 mass % or less.

To control the content of the hydrophilic polymer in the outer surface of the hollow fiber membrane within the above specified range, for example, the content of the hydrophilic polymer to the hydrophobic polymer is controlled within the above specified range; or otherwise, the conditions for forming the hollow fiber membranes are optimized. It is also an effective method to wash the hollow fiber membranes manufactured. In the manufacturing of the hollow fiber membranes, the humidity of the air gap portion of the outlet of a nozzle is adjusted; and the drawing conditions, the temperature of a solidifying bath, the composition ratio of a solvent to a non-solvent in a solidifying liquid, etc. are optimally controlled. The membranes are effectively washed with hot water or alcohol, or by centrifugation. Above all, the optimization of the humidity of the air gap portion and the composition ratio of the solvent to the non-solvent in the solidifying liquid, and the washing with alcohol as the washing method are particularly effective.

Preferably, the air gap portion is enclosed with a material capable of shielding the air gap from an external air. Preferably, the humidity of the inside of the air gap portion is controlled by the composition of a spinning dope, the temperature of the nozzle, the length of the air gap, the temperature of the external solidifying bath and the composition of the liquid. For example, a spinning dope of the following composition is extruded from a nozzle heated to a temperature of 30 to 60° C., and the resultant fibers are allowed to pass through the air gap with a length of 100 to 1,000 mm, and are then introduced into an external solidifying bath of a temperature of 50 to 80° C., wherein the ratio of the spinning dope is as follows: polyethersulfone/polyvinyl pyrrolidone/dimethylacetoamide/RO water=10 to 25/0.5 to 12.5/52.5 to 89.5/0 to 10.0. In this case, the absolute humidity of the air gap portion induces a dried air (0.01 to 0.3 kg/kg). By controlling the humidity of the air gap portion within the above specified range, the rate of hole area, the average hole area and the content of the hydrophilic polymer of the outer surface of the membrane can be controlled within proper ranges, respectively.

As the internal solidifying liquid, an aqueous solution of dimethylacetoamide (DMAc) (0 to 80 mass %) is preferred. When the concentration of the internal solidifying liquid is too low, the dense layer of the inner surface of the hollow fiber membrane becomes thick, which may lead to a lower solute permeability. The concentration of the internal solidifying liquid is more preferably 15 mass % or more, still more preferably 25 mass % or more, particularly 30 mass % or more. When this concentration is too high, the dense layer tends to be formed incompletely, and thus tends to have a lower fractional property. The concentration of the internal solidifying liquid is more preferably 70 mass % or less, still more preferably 60 mass % or less, particularly 50 mass % or less.

As the external solidifying liquid, an aqueous solution of 0 to 50 mass % of DMAc is preferably used. When the concentration of the external solidifying liquid is too high, the rate of hole area and the average hole area of the outer surface of the membrane become too large, which may induce more possibility of the back flow of endotoxin into the side of blood, or the decrease of the burst pressure during a dialysis. Accordingly, the concentration of the external solidifying liquid is more preferably 40 mass % or less, still more preferably 30 mass %, particularly 25 mass % or less. When this concentration is too low, it is needed to use a large amount of water to dilute the solute brought from the spinning dope, and the cost for treating the waste liquid becomes higher. Therefore, the lower limit of the concentration of the external solidifying liquid is more preferably 3 mass % or more, still more preferably 5 mass % or more.

In manufacturing the hollow fiber membranes of the present invention, preferably, the membranes are not substantially drawn before the structures of the hollow fiber membranes are completely fixed. The passage "the membranes are not substantially drawn" means that the speeds of rolls are controlled in the spinning step so that the spinning dope extruded from the nozzle is not loosen or excessively pulled. The ratio of the linear speed of extrusion to the speed of the first roll in the solidifying bath (draft ratio) is preferably 0.7 to 1.8. When the draft ratio is too low, the hollow fiber membranes being fed are loosen, which may lead to lower productivity. Therefore, the draft ratio is more preferably 0.8 or more, still more preferably 0.9 or more, particularly 0.95 or more. When the draft ratio is too large, the dense layers of the hollow fiber membranes are spilt and thus, the structures of the membranes may be destructed. Therefore, the draft ratio is more preferably 1.7 or less, still more preferably 1.6 or less, particularly 1.5 or less, most preferably 1.4 or less. By controlling the draft ratio within this range, the deformation or destruction of the holes of the membranes can be prevented, and the holes of the membranes are not clogged with the protein in blood. As a result, the membranes can exhibit performance stability and sharp fractional properties.

The hollow fiber membranes having passed through a water bath are wound onto a hank in the wet state, to thereby form a bundle of 3,000 to 20,000 membranes. The resultant bundle of hollow fiber membranes is washed to remove the excessive solvent and hydrophilic polymer. In the present invention, the bundle of hollow fiber membranes is preferably washed by dipping the same in hot water of 70 to 130° C. or an aqueous solution of 10 to 40 vol. % of ethanol or isopropanol of a room temperature to 50° C. Also, the following washing methods are also preferred.

(1) In case of washing with hot water, the bundle of hollow fiber membranes is dipped in excessive RO water and treated therein at a temperature of 70 to 90° C. for 15 to 60 minutes. Then, the bundle thereof is removed and subjected to centrifugal hydroextraction. This operation is repeated three or four times for washing, while the RO water is replaced.
(2) Otherwise, the bundle of hollow fiber membranes dipped in excessive RO water in a compressed container may be treated at 121° C. for about 2 hours.
(3) The same operation as the above operation (1) is preferably repeated, when an aqueous solution of ethanol or isopropanol is used.
(4) The bundle of hollow fiber membranes is radially arranged in a centrifugal washing machine, and is then subjected to centrifugal washing for 30 minutes to 5 hours in total, while a washing liquid of 40 to 90° C. is being shower-like blown onto the bundle from the center of rotation.

Two or more of the above methods may be combined. When the treating temperature is too low, it may be needed to increase the number of washing, in any of the above methods, which results in higher cost. When the treating temperature is too high, the decomposition of the hydrophilic polymer is accelerated, which, on the contrary, may lower the washing efficiency. By this washing, it becomes possible to properly adjust the content of the hydrophilic polymer in the outer surfaces of the membranes and to inhibit the sticking of the membranes or to decrease the amount of the eluate.

In this regard, the content of the hydrophilic polymer in the outermost surface of the hollow fiber membrane is measured and calculated by the ESCA method as will be described later: that is, the absolute value of the content of the same polymer in the outermost surface of the hollow fiber membrane (with a depth of several to several tens Å from the surface layer) is determined. Generally, the ESCA method (the outermost layer) makes it possible to measure the content of the hydrophilic polymer (PVP) in the surface of the hollow fiber membrane, up to a depth of about 10 nm (100 Å) from the surface thereof.

Another feature of the present invention is that the burst pressure of the hollow fiber membranes set in the blood purifier is 0.5 MPa or higher, and the coefficient of water permeability of the blood purifier, 150 ml/m$^2$/hr./mmHg or higher. When the burst pressure is too low, it becomes impossible to detect a latent defect which leads to the leakage of blood as will be described later. When the coefficient of water permeability is too low, the dialysis efficiency becomes lower. It is effective to increase the hole size or increase the number of holes of the membrane, in order to improve the dialysis efficiency. However, this method has a problem in that the strength of the membranes decreases or in that the membranes have defects. In contrast, the hollow fiber membranes of the present invention have strength balanced with the resistance to the permeation of a solute, by optimizing the hole sizes of the outer surfaces of the membranes to thereby optimize the percentage of voids of the support layers. The coefficient of water permeability is more preferably 200 ml/m$^2$/hr./mmHg or more, still more preferably 300 ml/m$^2$/hr./mmHg or more, particularly 400 ml/m$^2$/hr./mmHg or more, and most preferably 500 ml/m$^2$/hr./mmHg or more. When the coefficient of water permeability is too large, the water-removing control during hemodialysis becomes difficult. Therefore, the coefficient of water permeability is preferably 2,000 ml/m$^2$/hr./mmHg or less, more preferably 1,800 ml/m$^2$/hr./mmHg or less, still more preferably 1,500 ml/m$^2$/hr./mmHg or less, particularly 1,300 ml/m$^2$/hr./mmHg or less, and most preferably 1,000 ml/m$^2$/hr./mmHg or less.

The present inventors have studied the physical properties of hollow fiber membranes suitable for use in a blood purifier. Generally, a blood purifier is subjected to a leak test by way of compressing the internal or external portions of the hollow fiber membranes with an air, in the final stage for finishing a product, so as to check the defects of the hollow fiber membrane and a module. When any leakage is detected by the compressed air, the module is scrapped as a defective, or such defects of the module are repaired. The air pressure for use in this leak test is often several times larger than the proof pressure (generally 500 mmHg (0.067 MPa)) of a hemodialyzer. The present inventors have found that the very fine flaws, crushing or splitting of hollow fiber membranes having very high water permeability, which can not be detected by any of conventional compression leak tests, cause the cutting or pin holes of the hollow fiber membranes, in the course of the manufacturing steps after the leak test (mainly in the step of sterilization or packing), in the course of transporting, or in the course of handling in a clinical site (unpacking or priming); and they also have found that such cutting or pin holes in the membranes cause troubles such as the leakage of blood during a therapy. As a result of the inventors' intensive researches about this problem, it is found that the pressure of the compressed air for use in the conventional leak tests is insufficient to detect such latent defects of hollow fibers that lead to the occurrence of cutting or pin holes of the hollow fiber membranes in use for a clinical treatment. Then, the present inventors have found that a still higher pressure is needed to detect such latent defects, and that it is effective to prevent the occurrence of the non-uniform thickness of the hollow fiber membranes, in order to avoid the occurrence of the above latent defects. The present invention is accomplished based on such findings.

The burst pressure referred to in the present invention is used as an index for the pressure-resisting performance of hollow fiber membranes in a module made up of the hollow fibers: the burst pressure is a pressure which bursts the hollow fiber membranes, when the interiors of the hollow fiber membranes are compressed with a gas while the applied pressure is being gradually increased until the hollow fiber membranes can not withstand their internal pressures and are finally burst. The burst pressure is preferably 0.5 MPa or higher, more preferably 0.55 Mpa or higher, particularly 0.6 MPa or higher, since the possibility of causing cutting or pin holes in the hollow fiber membranes in use becomes lower, when the burst pressure is higher. When the burst pressure is excessively low, the hollow fiber membranes may have possible latent defects. However, desired membrane performance may not be obtained, when the thickness of the membranes is increased or when the void ratio is excessively decreased, in order to increase the burst pressure, although a higher and higher burst pressure is desirable. When hemodialysis membranes are intended, the burst pressure of the membranes is preferably below 2.0 MPa, more preferably below 1.7 MPa, still more preferably 1.5 MPa or lower, still more preferably below 1.3 MPa, particularly below 1.0 MPa.

The present invention is accomplished also based on the finding that the safety of the conventional hollow fiber membranes can not be reliably ensured over a long period of dialysis therapy because of the blood leakage therefrom which occurs depending on the macro properties such as the strength of known membranes or the like. To ensure the safety of the membranes against the blood leakage over a long period of dialysis therapy, the present inventors have intensively studied in order to establish an evaluation method for detecting the above-described latent defects in addition to the macro properties of membranes. As a result of such efforts, the present invention is accomplished.

The non-uniformity herein referred to in the present invention means the non-uniform thickness of the partial sections of 100 hollow fiber membranes in a hollow fiber membrane module, when the sections of the hollow fiber membranes are observed. The non-uniformity is indicated by a ratio of a maximum value to a minimum value. The present invention is characterized in that the minimum non-uniformity of 100 hollow fibers is 0.6 or more. When even only one hollow fiber having a non-uniformity of smaller than 0.6 is included in 100 follow fibers, such a hollow fiber has a danger of causing the leakage of blood during a clinical therapy. Therefore, the non-uniformity referred to in the present invention is not an average value but a minimum value among the values of non-uniformity of the 100 follow fibers. The higher the non-uniformity, the better, because the uniformity of the membranes is improved so that the manifestation of latent defects of the membranes is suppressed to thereby increase the burst pressure. The non-uniformity is more preferably 0.7 or more, still more preferably 0.8 or more, particularly 0.85 or more. When the non-uniformity is too low, the latent defects of the membranes tend to occur as actual defects, so that the burst pressure becomes lower and that the leakage of blood from the membranes tends to occur.

The thickness of the hollow fiber membranes is preferably 10 to 60 µm. When this thickness is too large, the permeability of a polymer which has a medium or high molecular weight and which immigrates at a low speed may become lower, although the water permeability of the membranes is high. As the membranes become thinner and thinner, the substance-permeability becomes higher. Thus, the thickness of the membrane is more preferably 55 µm or less, still more preferably 50 µm or less, particularly 47 µm or less. When the thickness of the membranes is too small, the strength of the membranes is low, and the burst pressure becomes lower even if the non-uniformity is 0.6 or more. Therefore, the thickness of the membranes is more preferably 20 µm or more, still more preferably 25 µm or more, particularly 30 µm or more, most preferably 35 µm or more.

The hollow fiber membranes of the present invention are suitable for use as hollow fiber membranes for hemocatharsis, and particularly suitable for use as hollow fiber membranes for the therapy of renal failure, such as hemodialysis, hemodiafiltration, hemofiltration or the like.

The hollow fiber membranes for use in a blood purifier are preferably manufactured by a dry process using a solution of the blend of a hydrophobic polymer and a hydrophilic polymer at the foregoing composition ratio, in a solvent. As mentioned above, it is effective to control the non-uniformity of the hollow fiber membranes to 0.6 or more in order to increase the burst pressure to 0.5 MPa or higher. To control the non-uniformity of the membrane to 0.6 or more, for example, it is preferable to strictly uniform the width of the slit of a nozzle which is an outlet for discharging the membrane-forming solution. Generally used as a spinning nozzle for hollow fiber membranes is a tube-in-orifice type nozzle having an annular portion for discharging a spinning dope, and a hole for injecting a core solution which is a hollow portion-forming agent, inside the annular portion. The width of the slit indicates the width of the outer annular portion for discharging the spinning dope. By lessening the variation in the width of the slit, the non-uniformity of the thickness of a spun hollow fiber membrane can be decreased. Specifically, the ratio of a maximum value to a minimum value of the width of the slit is controlled to 1.00 to 1.11, and preferably, the difference between the maximum value and the minimum value is adjusted to preferably 10 µm or less, more preferably 7 µm or less, still more preferably 5 µm or less, particularly 3 µm or less. In addition, the temperature of the nozzle is optimized: the temperature of the nozzle is preferably 20 to 100° C. When the temperature of the nozzle is too low, the nozzle is susceptible to the influence of a room temperature, and the temperature thereof is not steady, so that discharge spots of the spinning dope often occur. Accordingly, the temperature of the nozzle is more preferably 30° C. or higher, still more preferably 35° C. or higher, far more preferably 40° C. or higher. When the temperature of the nozzle is too high, the viscosity of the spinning dope excessively lowers, so that the steady discharge of the spinning dope may be impossible, and that the thermal deterioration or decomposition of the hydrophilic polymer may proceed. Therefore, the temperature of the nozzle is more preferably 90° C. or lower, still more preferably 80° C. or lower, particularly 70° C. or lower.

To further increase the burst pressure, the flaws of the surfaces of the hollow fiber membranes and the inclusion of foreign bodies and bubbles are lessened to thereby decrease the latent defects of the membranes. To prevent the occurrence of flaws on the membranes, it is effective to optimize the materials for rollers and guides used in the steps of manufacturing hollow fiber membranes, and the roughness of the surfaces thereof. It is also effective to decrease the number of times of contact between a module casing and the hollow fiber membranes or the number of frictions between each of the hollow fiber membranes, when the bundle of the hollow fiber membranes is set in the module casing to assemble the module. In the present invention, the rollers to be used is preferably planished at their surfaces in order to prevent the hollow fiber membranes from slipping and having flaws on the surfaces thereof. The surfaces of the guides to be used are preferably matte-finished or knurly finished to avoid the contact with the hollow fiber membranes as much as possible. The bundle of hollow fiber membranes is not directly inserted into the module casing, but preferably, the bundle of hollow fiber membranes wrapped in a matte-finished film is inserted in the module casing, and then, only the film is removed from the module casing.

To prevent the hollow fiber membranes from including foreign bodies, it is effective to use materials containing less foreign bodies, or to decrease the amount of foreign bodies by filtering the spinning dope for forming the membranes. In the present invention, the spinning dope is filtered through a filter having holes with a diameter smaller than the thickness of the hollow fiber membranes. Specifically, a spinning dope which is homogeneously dissolved is allowed to pass through a sintered filter which has holes with diameters of 10 to 50 μm and which is located on a passage along which the spinning dope is guided from a dissolution tank to a nozzle. The filtering may be done at least once, however, it is preferable to make the filtering treatment in a plurality of steps in order to improve the filtering efficiency and to prolong the life of the filter. The diameter of the holes of the filter is preferably 10 to 45 μm, more preferably 10 to 40 μm, still more preferably 10 to 35 μm. When the diameter of the holes of the filter is too small, the back pressure increases, and the quantitative evaluation may degrade.

To prevent the inclusion of bubbles in the membranes, it is effective to degass the polymer solution for forming membranes. Stationary degassing or decompression degassing may be employed in accordance with the viscosity of the spinning dope. In concrete, the inner space of a dissolution tank is decompressed to −100 to −750 mmHg, and then is sealed, and the tank is left to stand in a still state for 5 to 30 minutes. This operation is repeated several times for degassing the tank. When the decompression degree is too low, it may be needed to increase the number of times of degassing, which requires longer time. When the decompression degree is too high, high cost may be required to improve the sealing degree of the system. The total time for the degassing treatment is preferably 5 minutes to 5 hours. When the treating time is too long, the hydrophilic polymer may be decomposed and deteriorated due to the decompression effect. When the treating time is too short, the effect of degassing may become poor.

In the present invention, preferably, the rate of hole area of the outer surface of the hollow fiber membrane is 8 to 25%, and the average hole area of the open area of the outer surface of the hollow fiber membrane is 0.3 to 1.0 μm$^2$, in order to impart the foregoing features to the membrane. When the rate of hole area and the average hole area are too small, the water permeability tend to lower. When the hollow fiber membranes are dried, the membranes are stuck to one another due to the hydrophilic polymer present on the outer surfaces of the membranes, which makes it hard to assemble the module. Therefore, the rate of hole area is more preferably 9% or more, still more preferably 10% or more. The average hole area is more preferably 0.4 μm$^2$ or more, still more preferably 0.5 μm$^2$ or more, far more preferably 0.6 μm$^2$ or more. On the contrary, when the rate of hole area and the average hole area are too large, the burst pressure tends to lower. Therefore, the rate of hole area is more preferably 23% or less, still more preferably 20% or less, particularly 17% or less, most preferably 15% or less. The average hole area is more preferably 0.95 μm$^2$ or less, still more preferably 0.90 μm$^2$ or less.

To control the content of the hydrophilic polymer to the hydrophobic polymer in the membrane within the foregoing range, for example, the composition ratio of the hydrophobic polymer to the hydrophilic polymer in the spinning dope is adjusted to 95:5 to 67:33; the condition for the external solidifying liquid is adjusted to 5 to 40 mass %; or the resultant membranes are washed with hot water or alcohol.

The present invention is accomplished by the present inventors' intensive researches for optimizing the content of the hydrophilic polymer in the outer surface of the hollow fiber membrane and for optimizing the burst pressure, as separate techniques. Surprisingly, they have found that an unexpected synergetic effect as will be described later is produced by simultaneously carrying out both the techniques which appear to be independently of each other. The present invention is achieved based on such a finding. Recently, hemodiafiltration has attracted public attentions in the hemodialysis therapy. The hemodiafiltration is invented in order to remove even low molecular weight proteins, by adding the effect of filtration to the conventional hemodialysis which is conducted mainly by making use of the effect of diffusion. In the hemodiafiltration, forced liquid replacement between blood and a dialyzate is conducted by inducing a large difference in pressure between the blood and the dialyzate under a pump load. Therefore, the hollow fiber membranes are required to have pressure resistance which the conventional membranes have not had. The latent defects of membranes which have not been considered so serious, therefore, may raise actual problems in the hemodiafiltration. The present inventors have discovered that the defects of membranes can be previously detected by increasing the burst pressure to a given value or more, so as to ensure the safety of the membranes as commercial products capable of sufficiently corresponding to the hemodiafiltration. In the hemodiafiltration, the liquid replacement between large amounts of blood and a dialyzate is conducted as mentioned above. In the blood inlet portion of the module, forward filtering proceeds in the direction from blood to a dialyzate, and in the blood outlet portion of the module, the dialyzate is caused to flow back because of backward filtration in the direction from the dialyzate to the blood. When endotoxin, etc. in the elute derived from the material of the hollow fiber membranes and the dialyzate are mixed into the blood during the therapy, there is a danger of inducing grave symptoms such as anaphylaxis, etc. In the hollow fiber membrane of the present invention, the amount of the hydrophilic polymer in the outer surface of the membrane is controlled within the specified range and the rate of hole area and the hole area of the surface of the membrane are controlled within the specified ranges. By doing so, no leakage of blood from the membrane occurs during the hemofiltration or the hemodiafiltration, even if the hollow fiber membrane has a high water permeability (having holes with large diameters and a high void ratio). Thus, the solute-removing performance of preventing the inclusion of foreign bodies into blood and the safety can be concurrently achieved at high levels.

EXAMPLES

Hereinafter, the effectiveness of the present invention will be explained by way of Examples thereof, which should not be construed as limiting the scope of the present invention in any way. The methods of evaluating the physical properties in the following Examples are described below.

1. Coefficient of Water Permeability

The circuit on the side of the blood outlet in a dialyzer (on the side of the outlet from a pressure-measuring point) was blocked with a forceps to make a full filtration circuit. A compression tank is charged with pure water maintained at 37° C., and the pure water is fed to the dialyzer insulated in a constant-temperature bath of 37° C. while the pressure in the bath is being controlled with a regulator, and the mass of a filtrate flowing out of the side of the dialyzate was measured in the order of up to $1/100$ g. The difference in pressure between each of the membranes (TMP) is expressed by the equation:

$$TMP=(Pi+Po)/2$$

[in the equation, Pi represents the pressure on the side of the inlet of the dialyzer; and Po, the pressure on the side of the outlet thereof]. The TMP was varied at four points, and the flow amount of the filtrate was measured, and the coefficient of water permeability (mL/hr./mmHg) was calculated from the gradient indicating the relationship between TMP and the flow amount of the filtrate. At this point of time, the coefficient of correlation between TMP and the flow amount of the filtrate must be 0.999 or more. To reduce an error in pressure loss due to the circuit, TMP was measured within a pressure range of 100 mmHg or lower. The coefficient of water permeability of the hollow fiber membrane was calculated from the area of the membrane and the coefficient of water permeability of the dialyzer:

$$UFR(H)=UFR(D)/A$$

[in the equation, UFR(H) represents the coefficient of water permeability ($mL/m^2/hr/mmHg$) of the hollow fiber membrane; and UFR(D), the coefficient of water permeability (mL/hr/mmHg) of the dialyzer; and A, the area ($m^2$) of the membrane in the dialyzer].

2. Calculation of the Area of Membranes

The area of membranes in a dialyzer was calculated based on the inner diameter of the hollow fiber membrane as a reference:

$$A=n \times \pi \times d \times L$$

[in the equation, n represents the number of hollow fiber membranes in the dialyzer; π represents the ratio of the circumference of a circle to its diameter; d represents the inner diameter (m) of the hollow fiber membrane; and L represents the effective length (m) of the hollow fiber membrane in the dialyzer].

3. Burst Pressure

A module comprising about 10,000 hollow fiber membranes, on the side of a dialyzate, was filled with water and was then capped. A dried air or nitrogen was fed from the side of blood at a room temperature so as to compress the hollow fiber membranes at a rate of 0.5 MPa/min. The pressure was increased so that the hollow fiber membranes were bursted by the compressed air. The air pressure was measured, when bubbles formed in the liquid filling the module on the side of the dialyzate, simultaneously with the bursting of the membranes. This air pressure was defined as a burst pressure.

4. Non-Uniformity of Thickness

The sections of 100 hollow fibers were observed through a projector of a magnification of 200. One hollow fiber which had portions whose sections had the largest difference in thickness was selected from 100 hollow fibers in one field of view, and the thickness of this hollow fiber was measured at its thickest portion and its thinnest portion.

The non-uniformity of thickness=the thickness of the thinnest portion/the thickness of the thickest portion In this regard, the thickness of a membrane is perfectly uniform when the non-uniformity of thickness is one.

5. Amount of Hydrophilic Polymer Eluted

A method of measuring the amount of polyvinyl pyrrolidone, as a hydrophilic polymer, eluted from a membrane is described.

Extraction was made on a membrane according to the method regulated in the approved criteria for manufacturing dialyzer type artificial kidney, and polyvinyl pyrrolidone in the extract was determined by a calorimetric method.

In detail, pure water (100 ml) was added to hollow fiber membranes (1 g), and extraction was made on the hollow fiber membranes at 70° C. for one hour. To the resultant extract (2.5 ml), a 0.2 mol aqueous citric acid solution (1.25 ml) and a 0.006N aqueous iodine solution (0.5 ml) were added, and the mixture was sufficiently mixed and was left to stand alone at a room temperature for 10 minutes. After that, the absorbance of the mixture was measured at 470 nm. The determination was made using polyvinyl pyrrolidone as a sample, based on the analytical curve determined according to the above method.

In case of a module comprising wet hollow fiber membranes, physiological saline (500 ml/min.) was allowed to pass through the passage on the side of dialyzate in the module at a rate of 500 mL/min. for 5 minutes, and then was allowed to pass through the passage on the side of blood in the module at a rate of 200 mL/min. After that, physiological saline was allowed to pass through for 3 minutes, while filtration was being made from the side of the blood to the side of the dialyzate. Then, the membranes were freeze-dried. The resultant dried membranes were used for determination.

6. Content of Hydrophilic Polymer in Outer Surface of Membrane

The content of a hydrophilic polymer to a hydrophobic polymer was determined by the X-ray photoelectron spectroscopy (ESCA method). Analysis using a polysulfone type polymer as a hydrophobic polymer and polyvinyl pyrrolidone as a hydrophilic polymer is herein described.

One hollow fiber membrane was applied on a sample table to be analyzed by the X-ray photoelectron spectroscopy (ESCA method). The conditions for the analysis are as follows:

Apparatus: ULVAC-PHI ESCA5800
Excitation X-ray: MgKα ray
X-ray output: 14 kV, 25 mA
Escape angle of photoelectron: 45°
Analyzed diameter: 400 μmφ
Pass energy: 29.35 eV
Resolution: 0.125 eV/step
Degree of vacuum: about $10^{-7}$ Pa or less The content of PVP in the surface of the membrane was calculated from the found value of nitrogen (N) and the found value of sulfur (S), by the following equation (herein, the molecular weight of polyvinyl pyrrolidone is 111; that of polyether sulfone, 232; and that of polysulfone, 442).

<Membrane of PES (Polyether Sulfone) Admixed with PVP>

Content of PVP (Hpvp) [mass %]=100×(N×111)/(N× 111+S×232)

<Membrane of PSf (polysulfone) Admixed with PVP>

Content of PVP (Hpvp) [mass %]=100×(N×111)/(N× 111+S×442)

7. Content of Hydrophilic Polymer in Membrane

Measurement using PVP as a hydrophilic polymer is described as one of examples. A sample was dried with a vacuum drier at 80° C. for 48 hours, and 10 mg of the dried sample was analyzed with a CHN coder (Model MT-6, manufactured by YANAKO BUNSEKI KOGYOSHA). The content of PVP was calculated from the content of nitrogen by the following equation.

The content of PVP (mass %)=the content of nitrogen (mass %)×111/14

8. Rate of Hole Area of Outer Surface of Hollow Fiber Membrane

The outer surface of a hollow fiber membrane was observed with an electron microscope of a magnification of 10,000 and photographed (SEM photograph). The obtained image is processed with an image analysis processing software to determine the rate of hole area of the outer surface of the hollow fiber membrane. For example, "Image Pro Plus" (Media Cybernetics, Inc.) is used as the image analysis processing soft for measurement. The fetched image was subjected to an emphasis filter operation so as to discriminate the hole portions from the closed portions. After that, the number of the holes was counted. If polymer chains of the lower layer are observed in the interiors of the holes, such holes were combined and regarded as one hole. The total (B) of the area (A) within the measured range and the area of the holes within the measured range was calculated, and the rate of hole area (%) was calculated by the equation: the rate of hole area (%)=B/A×100. This calculation was repeated with respect to 10 fields of view, and an average of the results was found. Scale-setting is carried out as the initiating operation, and the holes on the boundary around the measured range are not excluded from the counting.

9. Average Hole Area of Open Area of Outer Surface of Hollow Fiber Membrane

Counting was made in the same manner as in the above operation, to calculate the area of each hole. The holes on the boundary around the measured range were excluded from the counting. This calculation was repeated with respect to 10 fields of view, and an average of all the hole areas was calculated.

10. Thickness of Hollow Fiber Membrane

The sections of hollow fiber membranes were projected with a projector of a magnification of 200. The inner diameters (A) and the outer diameters (B) of the hollow fibers with maximum, minimum and medium sizes within each field of view were measured, and the thickness of each hollow fiber membrane was calculated by the following calculation, and an average of the thicknesses of 90 hollow fiber membranes within 30 fields of view was calculated.

The thickness of the membrane=$(B-A)/2$

11. Concentration of Endotoxin

A dialyzate containing endotoxin at a concentration of 200 EU/L was fed from the dialyzate inlet of a module at a rate of 500 ml/min. so as to filter the endotoxin-containing dialyzate from the outer side of a hollow fiber membrane to the inner side thereof at a filtering rate of 15 ml/min. for 2 hours. The filtered dialyzate thus obtained was reserved, and the concentration of endotoxin in the reserved dialyzate was measured. The concentration of endotoxin was analyzed with a limulus ESII test wako (manufactured by Wako Pure Chemical Industries, Ltd.) according to the method (gelation-reversing method) described in the manual attached thereto.

12. Blood Leak Test

Bovine blood of which the coagulation is inhibited by the addition of citric acid was fed to a blood purifier comprising a module primed with physiological saline, at a rate of 200 mL/min., and was filtered at a rate of 20 mL/min. The resulting filtrate was returned to the blood to render a circulating system. After 60 minutes has passed, the filtrate of the blood purifier was collected, and the reddish tone of the filtrate due to the leakage of blood cell was visually observed. This blood leak test was conducted using 30 blood purifiers in each of Examples and Comparative Examples, and the number of modules from which blood was leaked was investigated.

13. Sticking Tendency of Hollow Fiber Membranes

About 10,000 hollow fibers were bundled, and the bundle thereof was set in a module casing of 30 to 35 mmφ. The module casing was sealed with a two-component polyurethane resin to make up a module. The leak test was conducted on 5 standard modules for each size. After that, the number of the modules having defects in the sealing with the urethane resin was counted.

Example 1

Polyether sulfone (SUMIKAEXCEL(R)5200P, manufactured by Sumika Chem Tex Co., Ltd.) (17 mass %), polyvinyl pyrrolidone (COLIDONE(R)K-90 manufactured by BASF) (2.5 mass %), dimethylacetamide (DMAc) (77.5 mass %) and RO water (3 mass %) were homogeneously dissolved at 50° C., and then, the system was vacuumed up to −500 mmHg with a vacuum pump. After that, the system was immediately sealed so as not to change the composition of the membrane-forming solution due to the evaporation of the solvent or the like, and the system in this state was left to stand alone for 15 minutes. This operation was repeated three times so as to degas the membrane-forming solution. This solution was allowed to pass through sintered filters with hole sizes of each 15 µm in two stages, and then was injected through a tube-in-orifice nozzle heated to 80° C., using an aqueous solution of DMAc (60 mass %) as a void-forming agent which had been previously degassed for 30 minutes under a pressure of −700 mmHg. Then, the solution was allowed to pass through a drying section with a length of 400 mm, which was blocked from an outer air by a spinning tube, and then was solidified in the aqueous solution of DMAc (20 mass %) heated to 60° C. The resultant membrane in a wet state was directly wound onto a hank. The slit of the tube-in-orifice nozzle used had an average width of 60 µm, a maximum width of 61 µm and a minimum width of 59 µm, and the ratio of the maximum value to the minimum value of the width of the slit was 1.03. The draft ratio of the membrane-forming solution was 1.06. The absolute humidity of the drying section was 0.21 kg/kg dry air.

The bundle of about 10,000 hollow fiber membranes as obtained above was wrapped in a polyethylene film which was matte-finished at its surface on the side of the bundle, and then was washed in hot water of 80° C. for 30 minutes. This washing was repeated 4 times. After the completion of washing, the bundle of the membranes was dried under a nitrogen atmosphere of 40° C. The rollers used, with which the hollow fiber membranes came into contact during the spinning step, were planished at their surfaces, and all the guides used were matte-finished at their surfaces. The inner diameter of the resultant hollow fiber membrane was 198.5 μm, and the thickness of the membrane was 28.5 μm. The content of the hydrophilic polymer in the hollow fiber membrane was measured. As a result, the content thereof was 4.3 mass %.

A blood purifier was assembled using the hollow fiber membranes thus obtained, and was used for leak tests. As a result, no failure in adhesion, attributed to the sticking of the hollow fiber membranes, was observed.

The blood purifier was filled with RO water previously degassed, and was irradiated with γ-rays of 25 kGy for crosslinking the module. After the γ-ray irradiation, the hollow fiber membranes were cut out from the blood purifier, and the cut pieces of the hollow fiber membranes were subjected to an elution test. As a result, the amount of the eluted PVP was 8 ppm, which raised no problem.

The blood purifiers were charged with a compressed air under a pressure of 0.1 MPa, and several of the blood purifiers which showed decrease of 30 mmAq or less in pressure in 10 seconds were regarded as non-defective to the leak test, and such blood purifiers were used in the following test. The outer surface of the hollow fiber membrane removed from the blood purifier was observed with a microscope. As a result, no defect such as flaws or the like was observed. A fresh bovine blood admixed with citric acid was allowed to pass through the blood purifier at a flow rate of 200 mL/min. and at a filtering rate of 10 mL/min. As a result, no leakage of blood cell was observed. The amount of the endotoxin filtered from the outside of the hollow fiber membrane to the inside thereof was smaller than the limit for detection, which was the level of no problem. The results of other analyses are shown in Table 1.

Comparative Example 1

A bundle of wet hollow fiber membranes was obtained in the same manner as in Example 1, except that the same membrane-forming solution as that of Example 1 was not allowed to pass through a filter, and that the resultant membranes were not washed. The hollow fiber membranes thus obtained were used to assemble a blood purifier. The blood purifier was filled with RO water, and irradiated with γ-rays with an absorbed dose of 25 kGy so as to crosslink the module. The inner diameter of the resultant hollow fiber membrane was 199.3 μm, and the thickness thereof was 28.7 μm. The content of the hydrophilic polymer in the hollow fiber membrane was measured, and it was 9.6 mass %. The hollow fiber membranes were removed from the blood purifier after the irradiation with γ-rays, and observed with a microscope. As a result, some of the membranes had knob-like defects which seemed to occur due the inclusion of insoluble components. The blood purifier was charged with a compressed air under a pressure of 0.1 MPa, and modules which showed decrease of 30 mmAq or less in pressure in 10 seconds were used in tests. In the blood leak tests using bovine blood, the blood leaked from three out of thirty modules. This was because the thin portions of such modules had insufficient strength and/or some defects due to the non-uniformity in thickness and the low burst pressures. As a result of the endotoxin-permeating tests, endotoxin having permeated to the inner side of the hollow fiber membranes was observed. This was because, since no washing was done, the contents of PVP in the outer surface of the hollow fiber membranes increased, which made it easy for the endotoxine to pass through the membranes. The results of other analyses are shown in Table 1.

Comparative Example 2

Polyethersulfone (SUMICAEXEL(R)5200P, manufactured by SUMIKA CHEM TEX) (16 mass %), polyvinyl pyrrolidone (KOLIDONE(R)K-90, manufactured by BASF) (6 mass %), DMAc (75 mass %) and water (3 mass %) were dissolved at 50° C. The interior space of the system was decompressed up to −500 mmHg with a vacuum pump, and then was immediately sealed so as not to change the composition of the membrane-forming solution due to the evaporation of the solvent or the like. Then, the system was left to stand alone for 15 minutes. This operation was repeated three times to degas the membrane-forming solution. This solution was allowed to pass through a filter with a hole size of 100 μm, and then was extruded together with an aqueous solution of DMAc (30 mass %) as a void-forming agent which had been previously degassed under a pressure of −700 mmHg for 2 hours, through a tube-in-orifice nozzle heated to 60° C. The resultant semi-solid hollow fiber membrane was allowed to pass through a drying section with a length of 600 mm shielded with a spinning tube from an external and then was solidified in an aqueous solution of DMAc (concentration: 10 mass %) of 60° C. The slit of the tube-in-orifice nozzle used had an average width of 100 μm, a maximum width of 110 μm and a minimum width of 90 μm; the ratio of the maximum value to the minimum value of the width of the slit was 1.22; and the draft ratio was 2.41. The absolute humidity of the drying section was 0.11 kg/kg dry air. The resultant hollow fiber membrane was allowed to pass through a water bath of 40° C. for 45 seconds so as to remove the solvent and an excess of the hydrophilic polymer, and then was directly wound up in a wet state, and dried in an air at 50° C. The inner diameter of the resultant hollow fiber membrane was 197.8 μm, and the thickness of the membrane was 29.2 μm. The content of the hydrophilic polymer in the hollow fiber membrane was 7.4 mass %.

A blood purifier was assembled using the hollow fiber membranes thus obtained. The blood purifier was filled with pure water and irradiated with γ-rays of 25 kGy absorbed dose for crosslinking the module. The hollow fiber membranes were cut out from the blood purifier after the irradiation with γ-rays and subjected to an elution test. As a result, the amount of the eluted PVP was 12 ppm. This was because of the insufficient washing of the hollow fiber membranes. The blood purifier was charged with a compressed air under a pressure of 0.1 MPa to select modules which showed decrease of 30 mmAq or less in pressure in 10 seconds, and such modules were used in tests. Blood cell was leaked from two out of 30 modules in the blood leak tests using bovine blood. It is considered that this was attributed to the occurrence of pin holes and/or breakage of the membranes because of the small non-uniformity and the too large sizes of the holes in the outer surfaces of the membranes. As a result of the endotoxin-permeating tests, endotoxin filtered from the outside of the hollow fibers to the inside thereof was detected. It is supposed that the larger amount of PVP in the outer surface of the membrane and the higher rate of hole area of the membrane facilitated the permeation of endotoxin. The results of other analyses are shown in Table 1.

Example 2

Polyether sulfone (SUMIKAEXCEL(R)4800P, manufactured by Sumika Chem Tex Co., Ltd.) (18 mass %), polyvinyl pyrrolidone (COLIDONE(R)K-90 manufactured by BASF) (3.5 mass %), dimethylacetoamide (DMAc) (73.5 mass %) and water (5 mass %) were dissolved at 50° C. Then, the system was vacuumed up to −700 mmHg with a vacuum pump. After that, the system was immediately sealed so as not to change the composition of the membrane-forming solution due to the evaporation of the solvent or the like, and the system in this state was left to stand alone for 10 minutes. This operation was repeated three times to degas the membrane-forming solution. This solution was allowed to pass through filters with hole sizes of each 15 μm in two stages, and then was extruded through a tube-in-orifice nozzle heated to 70° C., together with an aqueous solution of DMAc (50 mass %) as a void-forming agent, which had been previously degassed for 2 hours under a pressure of −700 mmHg. Then, the solution was allowed to pass through an air gap with a length of 300 mm, which was blocked from an external air with a spinning tube, and then was solidified in water of 60° C. The slit of the tube-in-orifice nozzle used had an average width of 45 μm, a maximum width of 45.5 μm and a minimum width of 44.5 μm, and the ratio of the maximum value to the minimum value of the width of the slit was 1.02. The draft ratio of the membrane-forming solution was 1.06. The absolute humidity of the drying section was 0.12 kg/kg, which indicated a dry air. The hollow fiber membrane removed from the solidifying bath was allowed to pass through a water-washing bath of 85° C. for 45 seconds to remove the solvent and an excess of the hydrophilic polymer. After that, the resultant membrane was wound onto a hank. The rollers used to change the fiber path in the spinning step were planished at their surfaces, and the stationary guides were matte-finished at their surfaces.

The bundle of 10,000 hollow fiber membranes as obtained above was wrapped in the same polyethylene film as that used in Example 1, and then was dipped and washed in an aqueous solution of isopropanol (40 vol. %) of 30° C. for 30 minutes. This operation was repeated twice, and then, the bundle of the membranes was washed with water with which the aqueous isopropanol solution was replaced. After the completion of washing, the bundle of the membranes was dried under a nitrogen stream of 60° C. The inner diameter of the resultant membrane was 198.5 μm, and the thickness thereof was 28.5 μm. The content of the hydrophilic polymer in the hollow fiber membrane was measured. As a result, the content thereof was 7.3 mass %. A blood purifier was assembled using the hollow fiber membranes thus obtained, and was used for a leak test. As a result, no failure in adhesion, attributed to the sticking of the hollow fiber membranes, was observed. The blood purifier was used in the following analysis, without crosslinking the module. The hollow fiber membranes were cut out from the blood purifier which had been irradiated with γ-rays, and were subjected to an elution test. As a result, the amount of the eluted PVP was 6 ppm, which was evaluated as good. Further, the hollow fiber membranes were removed from the blood purifier, and the outer surfaces thereof were observed with a microscope. As a result, no defect such as flaws or the like was observed. In the blood leak test using bovine blood, any of the membranes showed no leakage of blood cell. As a result of the endotxin-permeating test, the amount of the endotoxin filtered from the outside of the hollow fibers to the inside thereof was smaller than the limit for detection, which was within the level of no problem. The results of other analyses are shown Table 1.

Comparative Example 3

Polyethersulfone (SUMICAEXEL(R)7800P, manufactured by Sukika Chem Tex Co., Ltd.) (22 mass %), polyvinyl pyrrolidone (KOLIDONE(R)K-30, manufactured by BASF) (9 mass %), DMAc (66 mass %) and water (3 mass %) were dissolved at 50° C. The interior of the system was decompressed up to −350 mmHg with a vacuum pump, and then was immediately sealed so as not to change the composition of the membrane-forming solution due to the evaporation of the solvent or the like, and then was left to stand alone for 30 minutes. This operation was repeated twice to degas the membrane-forming solution. The resultant solution was allowed to pass through filters with hole sizes of each 30 μm in two stages, and then was extruded together with an aqueous solution of DMAc (50 mass %) as a void-forming agent which had been previously degassed under reduced pressure, through a tube-in-orifice nozzle heated to 50° C. The resultant hollow fiber membrane was allowed to pass through an air gap with a length of 300 mm shielded with a spinning tube from an external air and then was solidified in water of 50° C. The slit of the tube-in-orifice nozzle used had an average width of 45 μm, a maximum width of 45.5 μm and a minimum width of 44.5 μm; the ratio of the maximum value to the minimum value of the width of the slit was 1.02; and the draft ratio was 1.06. The absolute humidity of the drying section was 0.07 kg/kg dry air. The resultant hollow fiber membrane removed from the above bath was allowed to pass through a water bath of 40° C. for 45 seconds so as to remove the solvent and an excess of the hydrophilic polymer, and then was wound up. The bundle of 10,000 hollow fiber membranes thus obtained were directly dried in an air at 40° C. without washing. The inner diameter of the resultant hollow fiber membrane was 199.5 μm, and the thickness thereof was 29.0 μm. The content of the hydrophilic polymer in the hollow fiber membrane was 7.7 mass %.

After the drying, some of the hollow fiber membranes in the bundle were stuck to one another. Thus, an adhesive resin was not successfully inserted between each of the hollow fiber membranes at their end portions, when a blood purifier was assembled using such hollow fiber membranes. Therefore, it was impossible to assemble the blood purifier. The results of the analysis are shown in Table 1.

Comparative Example 4

The same membrane-forming solution as that used in Example 1 was allowed to pass through filters with hole sizes of 30 μm and 15 μm, respectively, in two stages, and then was extruded together with an aqueous solution of DMAc (60 mass %) as a void-forming agent which had been previously degassed under reduced pressure, through a tube-in-orifice nozzle heated to 80° C. The resultant hollow fiber membrane was allowed to pass through a drying section with a length of 400 mm shielded with a spinning tube from an external air and then was solidified in a bath holding RO water of 70° C. The slit of the tube-in-orifice nozzle used had an average width of 60 μm, a maximum width of 62 μm and a minimum width of 58 μm; the ratio of the maximum value to the minimum value of the width of the slit was 1.07; and the draft ratio was 1.06. The absolute humidity of the drying section was 0.28 kg/kg dry air. The resultant hollow fiber membrane removed from the above bath was dipped in a water bath of 60° C. for 45 seconds, and then was wound up and dried in a hot air oven of 70° C. The inner diameter of the resultant hollow fiber membrane was 200.2 μm, and the thickness thereof was 30.5 μm. The content of the hydrophilic polymer in the hollow fiber membrane was 6.3 mass %.

A blood purifier was assembled using the hollow fiber membranes thus obtained, and was subjected to an air leak test. As a result, bubbles occurred from the adhered portion of the module comprising the hollow fiber membranes. It is considered that a failure in adhesion was attributed to the sticking of the hollow fibers. The hollow fiber membranes were cut out from the blood purifier which had not undergone a crosslinking treatment, and were subjected to an elution test. As a result, the amount of the eluted PVP was 12 ppm. It was considered that this result was attributed to the insufficient washing of the hollow fiber membranes and the non-crosslinked hydrophilic polymer. The above blood purifier was charged with a compressed air under a pressure of 0.1 MPa to select modules which showed decrease of 30 mmAq or less in pressure in 10 seconds, and such modules were used in tests. As a result of the blood leak test using bovine blood, no leakage of blood cell was observed. As a result of the endotoxin-permeating test, the concentration of endotoxin in the filtrate was 10 EU/L, which was a slightly high level. The results of the analysis of the blood purifier are shown in Table 1.

Comparative Example 5

Polyethersulfone (SUMIKAEXEL(R)5200P, manufactured by Sumika Chem Tex., Co., Ltd.) (17 mass %), polyvinyl pyrrolidone (KOLIDONE(R)K-90, manufactured by BASF) (7.5 mass %), DMAc (72.5 mass %) and water (3 mass %) were dissolved at 50° C. The interior of the system was decompressed up to −500 mmHg with a vacuum pump, and then was immediately sealed so as not to change the composition of the membrane-forming solution due to the evaporation of the solvent or the like, and then was left to stand alone for 30 minutes. This operation was repeated three times to degas the membrane-forming solution. The resultant membrane-forming solution was extruded together with an aqueous solution of DMAc (75 mass %) as a void-forming agent which had been previously degassed under reduced pressure, through a tube-in-orifice nozzle heated to 50° C., without filtering. The resultant hollow fiber membrane was allowed to pass through an air gap with a length of 600 mm, shielded with a spinning tube from an external air, and then was solidified in water of 70° C. The slit of the tube-in-orifice nozzle used had an average width of 60 μm, a maximum width of 64 μm and a minimum width of 56 μm; the ratio of the maximum value to the minimum value of the width of the slit was 1.14; and the draft ratio was 1.06. The absolute humidity of the drying section was 0.23 kg/kg dry air. The resultant hollow fiber membrane was washed with water to remove the solvent, and then was wound up to make up a bundle of about 10,000 hollow fiber membranes. Then, the bundle of the membranes was dipped in an aqueous solution of glyceline (30 mass %) of 50° C. for one hour and dried at 80° C. The inner diameter of the resultant hollow fiber membrane was 197.8 μm, and the thickness thereof was 30.3 μm. The content of the hydrophilic polymer in the hollow fiber membrane was 6.1 mass %.

The bundle of the hollow fiber membranes thus obtained showed no sticking of the hollow fibers, since the surfaces of the membranes were coated with glyceline. However, a blood purifier assembled using this bundle of the hollow fiber membranes could not ensure sufficient safety, because of the large amount of the urethane oligomer at the end portions of the hollow fibers. The blood purifier filled with water was irradiated with γ-rays of a 25 kGy absorbed dose. The hollow fiber membranes were cut out from the blood purifier after the γ-ray irradiation, and were subjected to an elution test. As a result, the amount of the eluted PVP was 13 ppm. It was considered that this result was attributed to the insufficient washing of the hollow fiber membranes and the influence of the glyceline in the filler liquid which hindered the crosslinking of the hydrophilic polymer. The above blood purifier was charged with a compressed air under a pressure of 0.1 MPa to select modules which showed decrease of 30 mmAq or less in pressure in 10 seconds, and such modules were used in tests. As a result of the blood leak tests using bovine blood, the leakage of blood cell was observed in four out of 30 modules. It was considered that this result was attributed to the small non-uniformity in thickness and the too large sizes of holes in the outer surfaces of the membranes. As a result of the endotoxin-permeating test, the concentration of endotoxin filtered from the outside of the hollow fibers to the inside thereof had a very high level. It was considered that this result was attributed to the large rate of hole area and the large hole area of the outer surfaces of the membranes. The results of other analyses are shown in Table 1.

Example 3

Polysulfone (P-3500, manufactured by AMOKO) (18 mass %), polyvinyl pyrrolidone (K-60 manufactured by BASF) (9 mass %), DMAc (68 mass %) and water (5 mass %) were dissolved at 50° C., and then, the system was vacuumed up to −300 mmHg with a vacuum pump. After that, the system was immediately sealed so as not to change the composition of the membrane-forming solution due to the evaporation of the solvent or the like, and the system in this state was left to stand alone for 15 minutes. This operation was repeated three times to degas the membrane-forming solution. This solution was allowed to pass through filters with hole sizes of each 15 μm in two stages, and then was extruded through a tube-in-orifice nozzle heated to 40° C., together with an aqueous solution of DMAc (35 mass %) as a void-forming agent which had been previously degassed under reduced pressure. Then, the resultant hollow fiber membrane was allowed to pass through an air gap with a length of 600 mm, which was blocked from an external air with a spinning tube, and then was solidified in water of 50° C. The slit of the tube-in-orifice nozzle used had an average width of 60 μm, a maximum width of 61 μm and a minimum width of 59 μm. The ratio of the maximum value to the minimum value of the width of the slit was 1.03, and the draft ratio was 1.01. The absolute humidity of the drying section was 0.06 kg/kg, which indicated a dry air. The hollow fiber membrane removed from the solidifying bath was allowed to pass through a water-washing bath of 85° C. for 45 seconds to remove the solvent and an excess of the hydrophilic polymer. After that, the resultant membrane was wound up to make up a bundle of about 10,000 hollow fiber membranes. The bundle of the hollow fiber membranes was dipped in pure water and washed in an autoclave at 121° C. for one hour. After the washing, the bundle of the membranes was wrapped in the same polyethylene film as that used in Example 1, and dried under a nitrogen stream of 45° C. The rollers used to change the fiber path in the spinning step were planished at their surfaces, and the stationary guides were matte-finished at their surfaces. The inner diameter of the resultant membrane was 201.2 μm, and the thickness thereof was 43.8 μm. The content of the hydrophilic polymer in the hollow fiber membrane was measured. As a result, the content thereof was 8.8 mass %.

A module was made up of the resultant hollow fiber membranes, and was used for a leak test. As a result, no failure in adhesion, attributed to the sticking of the hollow fibers, was observed. A blood purifier was assembled using the hollow fiber membranes thus obtained. The blood purifier was filled with RO water, and then was irradiated with γ-rays in a absorbed dose of 25 kGy to crosslink the module. The hollow fiber membranes were cut out from the blood purifier after the irradiation with γ-rays, and were subjected to an elution test. As a result, the amount of the eluted PVP was 7 ppm, which was in the level having no problem. The blood purifier was charged with compressed air under a pressure of 0.1 MPa to select modules which showed decrease of 30 mmAq or less in pressure, as accepted products to the leak tests, and such modules were used in the following tests. Further, the hollow fiber membranes were removed from the blood purifier, and the outer surfaces thereof were observed with a microscope. As a result, no defect such as flaws or the like was observed. Fresh bovine blood admixed with citric acid was allowed to pass through the blood purifier at a flow rate of 200 mL/min. and at a filtering rate of 10 mL/min. As a result, no leakage of blood cell was observed. The amount of the endotxin filtered from the outside of the hollow fibers to the inside thereof was smaller than the limit for detection, which was within the level of no problem. The results of other analyses are shown in Table 1.

Example 4

Polysulfone (P-1700, manufactured by AMOKO) (17 mass %), polyvinyl pyrrolidone (K-60 manufactured by BASF) (5 mass %), DMAc (73 mass %) and water (5 mass %) were dissolved at 50° C., and then, the system was vacuumed up to −400 mmHg with a vacuum pump. After that, the system was immediately sealed so as not to change the composition of the membrane-forming solution due to the evaporation of the solvent or the like, and the system in this state was left to stand alone for 30 minutes. This operation was repeated three times to degas the membrane-forming solution. This solution was allowed to pass through filters with hole sizes of each 15 μm in two stages, and then was extruded through a tube-in-orifice nozzle heated to 40° C., together with an aqueous solution of DMAC (35 mass %) as a void-forming agent which had been previously degassed under reduced pressure. Then, the resultant hollow fiber membrane was allowed to pass through an air gap with a length of 600 mm, which was blocked from an external air with a spinning tube, and then was solidified in water of 50° C. The slit of the tube-in-orifice nozzle used had an average width of 60 μm, a maximum width of 61 μm and a minimum width of 59 μm. The ratio of the maximum value to the minimum value of the width of the slit was 1.03, and the draft ratio was 1.01. The absolute humidity of the drying section was 0.07 kg/kg, which indicated a dry air. The hollow fiber membrane removed from the solidifying bath was allowed to pass through a water-washing bath of 85° C. for 45 seconds to remove the solvent and an excess of the hydrophilic polymer. After that, the resultant membrane was wound up to make up a bundle of about 10,000 hollow fiber membranes. The bundle of the hollow fiber membranes was dipped in pure water and washed in an autoclave at 121° C. for one hour. After the washing, the bundle of the membranes was wrapped in a polyethylene film, and dried under a nitrogen stream of 45° C. The rollers used to change the fiber path in the spinning step were planished at their surfaces, and the stationary guides were matte-finished at their surfaces. The inner diameter of the resultant hollow fiber membrane was 201.2 μm, and the thickness thereof was 43.8 μm. The content of the hydrophilic polymer in the hollow fiber membrane was measured. As a result, the content thereof was 5.2 mass %.

A module for use in evaluation was assembled using the resultant hollow fiber membranes, and was used for a leak test. As a result, no failure in adhesion, attributed to the sticking of the hollow fibers, was observed. A blood purifier was assembled using the hollow fiber membranes thus obtained. The blood purifier was filled with RO water, and irradiated with γ-rays in a absorbed dose of 25 kGy to crosslink the hydrophilic polymer. The hollow fiber membranes were cut out from the blood purifier after the irradiation with γ-rays, and were subjected to an elution test. As a result, the amount of the eluted PVP was 7 ppm, which was in the level having no problem. The blood purifier was charged with compressed air under a pressure of 0.1 MPa to select modules which showed decrease of 30 mmAq or less in pressure, as accepted products to the leak tests, and such modules were used in the following tests. Further, the hollow fiber membranes were removed from the blood purifier, and the outer surfaces thereof were observed with a microscope. As a result, no defect such as flaws or the like was observed. Fresh bovine blood admixed with citric acid was allowed to pass through the blood purifier at a flow rate of 200 mL/min. and at a filtering rate of 10 mL/min. As a result, no leakage of blood cell was observed. The amount of the endotxin filtered from the outside of the hollow fibers to the inside thereof was smaller than the limit for detection, which was within the level of no problem. The results of other analyses are shown in Table 1.

[Table 1]

TABLE 1

|  | Coefficient of water permeability | Burst pressure (MPa) | Non-uniformness | Leakage of blood | Eluted PVP (ppm) | Content of PVP in outer surface (%) |
|---|---|---|---|---|---|---|
| Ex. 1 | 510 | 0.6 | 0.71 | 0 | 8 | 33 |
| Ex. 2 | 342 | 0.6 | 0.90 | 0 | 6 | 27 |
| Ex. 3 | 602 | 0.7 | 0.82 | 0 | 7 | 29 |
| Ex. 4 | 290 | 0.6 | 0.88 | 0 | 7 | 32 |
| C. Ex. 1 | 498 | 0.2 | 0.47 | 3 | 8 | 51 |
| C. Ex. 2 | 526 | 0.3 | 0.41 | 2 | 12 | 52 |
| C. Ex. 3 | — | — | — | — | 14 | 57 |
| C. Ex. 4 | 488 | 0.7 | 0.72 | 0 | 12 | 44 |
| C. Ex. 5 | 502 | 0.2 | 0.43 | 4 | 13 | 48 |

|  | Rate of hole area (%) of outer surface | Av. hole area (μm$^2$) of outer surface | Number of membranes stuck to one another | Content of PVP in membrane (mass %) | Permeation of endotoxin | Insoluble component |
|---|---|---|---|---|---|---|
| Ex. 1 | 21 | 0.6 | 0 | 4.3 | ND | Some |
| Ex. 2 | 19 | 0.5 | 0 | 7.3 | ND | None |
| Ex. 3 | 13 | 0.8 | 0 | 8.8 | ND | Some |
| Ex. 4 | 24 | 0.9 | 0 | 5.2 | ND | Some |

TABLE 1-continued

| | | | | | | |
|---|---|---|---|---|---|---|
| C. Ex. 1 | 19 | 0.5 | 11 | 9.6 | X | Some |
| C. Ex. 2 | 32 | 1.2 | 0 | 7.4 | X | Some |
| C. Ex. 3 | 5 | 0.2 | 30 | 7.7 | — | None |
| C. Ex. 4 | 21 | 0.2 | 3 | 6.3 | X | None |
| C. Ex. 5 | 27 | 0.4 | 0 | 6.1 | X | Some |

Coefficient of water permeability: ml/m$^2$/hr./mmHg

INDUSTRIAL APPLICABILITY

The hollow fiber type blood purifiers of the present invention are highly reliable in safety and module-assembling ease, and are suitable for use as medical hollow fiber type blood purifiers which should exhibit high water-permeating performance for use in therapy of chronic renal failure.

The invention claimed is:

1. A highly water-permeable hollow fiber type blood purifier comprising hydrophobic polymer hollow fiber membranes, each of which contains a hydrophilic polymer,
wherein (i) the amount of the hydrophilic polymer eluted from the hollow fiber membrane is 10 ppm or less; (ii) the ratio of the hydrophilic polymer in the outer surface of the hollow fiber membrane is 25 to 50 mass %; (iii) the burst pressure of the hollow fiber membrane is 0.5 MPa or higher; (iv) the coefficient of water permeability of the blood purifier is 150 ml/m$^2$/hr./mmHg or higher; and (v) the average hole area of the outer surface of the hollow fiber membrane is 0.3 to 1.0 μm$^2$.

2. The highly water-permeable hollow fiber type blood purifier of claim 1, wherein the rate of hole area of the outer surface of the hollow fiber membrane is 8 to 25%.

3. The highly water-permeable hollow fiber type blood purifier of claim 1, wherein the hollow fiber membrane has a non-uniformity in thickness of 0.6 or more.

4. The highly water-permeable hollow fiber type blood purifier of claim 1, wherein the thickness of the hollow fiber membrane is 10 to 60 μm.

5. The highly water-permeable hollow fiber type blood purifier of claim 1, wherein the mass ratio of the hydrophilic polymer to the hydrophobic polymer is 1 to 20 mass %.

6. The highly water-permeable hollow fiber type blood purifier of claim 1, wherein the hydrophilic polymer is polyvinyl pyrrolidone.

7. The highly water-permeable hollow fiber type blood purifier of claim 1, wherein the hydrophilic polymer is crosslinked to be insoluble.

* * * * *